United States Patent [19]

Sanderson et al.

[11] Patent Number: 4,978,799

[45] Date of Patent: Dec. 18, 1990

[54] PRODUCTION OF DETERGENT RANGE ALCOHOLS AND KETONES USING PORPHYRIN CATALYSTS

[75] Inventors: John R. Sanderson, Leander; Edward T. Marquis; Howard F. Payton, both of Austin, all of Tex.

[73] Assignee: Texaco Chemical Company, White Plains, N.Y.

[21] Appl. No.: 428,812

[22] Filed: Oct. 30, 1989

[51] Int. Cl.$^5$ .............................................. C07C 45/28
[52] U.S. Cl. ................................. 568/385; 568/909.8; 568/910; 568/398.8
[58] Field of Search ..................... 568/385, 909.8, 910, 568/398.8

[56] References Cited

U.S. PATENT DOCUMENTS 3,816,548  6/1974  Williams et al. .................. 568/910
3,992,432  11/1976  Napier et al. ...................... 568/910

*Primary Examiner*—James H. Reamer
*Attorney, Agent, or Firm*—Jack H. Park; Kenneth R. Priem; David L. Mossman

[57] ABSTRACT

A process for the production of detergent range alcohols and ketones by reacting an alkane with a hydroperoxide in the presence of a transition metal porphyrin catalyst is described. Preferred hydroperoxides include cumene hydroperoxide and tertiary butyl hydroperoxide. The transition metal porphyrin catalyst may be transition metal phthalocyanines, transition metalloporphines and the like. The transition metal itself may be iron, manganese, cobalt and mixtures thereof. Suitable ligands include, but are not limited to imidazoles and lithium borate. Other useful additives include alkali metal perchlorates, such as sodium perchlorate, iodosylbenzene and alkali metal superoxides, such as potassium superoxide, and phase transfer catalysts such as tetrabutyl ammonium bromide.

11 Claims, No Drawings

PRODUCTION OF DETERGENT RANGE ALCOHOLS AND KETONES USING PORPHYRIN CATALYSTS

CROSS-REFERENCE TO RELATED APPLICATIONS

This application is related to U.S. patent application Ser. No 07/428,703, filed Oct. 30, 1989, relating to the production of detergent range alcohols and ketones from alkanes and hydroperoxides in the presence of transition metal acetylacetonate catalysts, and to U.S. patent application Ser. No. 07/428,701, filed Oct. 30, 1989, relating to the production of detergent range alcohols and ketones from alkanes and hydroperoxides in the presence of a dicyano bis-(1,10-phenanthrolene) iron (II) catalyst.

FIELD OF THE INVENTION

The invention relates to the catalytic production of detergent range alcohols and ketones and, in one aspect, more particularly relates to the production of detergent range alcohols and ketones from alkanes and hydroperoxides over a transition metal catalyst.

BACKGROUND OF THE INVENTION

Producing alcohols and/or ketones from alkanes and other co-reactants is known. Often, such technology is pursued in attempts to discover viable processes for making useful chemicals directly from hydrocarbons, anticipating dwindling petrochemical feedstocks. In other instances, the co-reactant may be a by-product from another process, and an economical way of converting the by-product to a useful material may be needed Sometimes a particular kind of alcohol or ketone, or mixture of alcohols and/or ketones is desired.

A number of publications provide a useful background in this technology. For example, A. N. Bashikirov, et al., in "Synthesis of Higher Aliphatic Alcohols by Direct Oxidation of Paraffinic Hydrocarbons," *Proc. World Pet. Cong.*, Vol. 4, (1959) pp. 175–183, report the "directed" synthesis of higher aliphatic alcohols via the liquid-phase oxidation of paraffinic hydrocarbons in the presence of boric acid, and by the selection of proper operating conditions which include a low oxygen concentration. Apparently, the boric acid serves as an esterification agent in the oxidation, and the conversion of alcohols into boric acid esters prevents them from further oxidation by interrupting the oxidative conversion chain at the alcohol stage. See also N. J. Stevens, et al., "A New Route for Alcohols," *Chemical Engineering Progress*, Vol. 64, No. 7, (1968) p. 61–66. Similarly, U.S. Pat. No. 3,243,449 teaches the oxidation of saturated hydrocarbons having 4 to 8 carbon atoms with molecular oxygen in the presence of metaboric acid or a less hydrated form of orthoboric acid, including boric anhydride, to produce borate esters. In this process, the contact temperature for the reactants is in the range of about 140° to 180° C., and the reaction is maintained so that the partial pressure of water in the exit gases, i.e., the vapor above the liquid reaction mixture, in psia is not greater than P, where P is given by the expression $\log_{10} P = 0.01112T - 0.259$.

In this same area is work reported by M. J. Ijam, et al., in "Liquid-Phase Oxidation of n-Dodecane in the Presence of Boron Compounds," *Ind. Eng. Chem. Prod. Res. Dev.*, Vol. 20, (1981) pp. 315–319. The paper describes experiments on the production of neutral oxidation products rich in alcohols by the direct air oxidation of n-dodecane in the presence of boron compounds, such as tributoxyboroxine, boron trioxide, dibutoxyborane, etc. As with some of the previously discussed publications, lean oxygen-nitrogen mixtures (4% oxygen) are also used, here giving a mixture of six possible straight-chain $C_{12}$ alcohols.

In the absence of boric or other like catalysts, the direct oxidation of hydrocarbons produces alcohols and ketones in usually less than 60% selectivity, even at conversions of 20–30% In the presence of boric acid, the selectivity to alcohols is increased to about 75–80% at 20–30% conversion, but even here, there are carboxylic acids and other by-products produced In addition, the 10 hydrolysis of the borate esters and isolation of the products is not a simple operation.

Paraffins having four to eight carbon atoms may be oxidized in the liquid phase with molecular oxygen in a reactor in which the manganese content is maintained in the range of 2 to 50 ppm to produce carboxylic acids, according to U.S. Pat No. 3,859,346. The manganese may be in the form of manganese salts of carboxylic acids, e.g. manganese naphthenate, or in an aqueous solution, e.g. manganese acetate.

Also of general interest is "Porphyrin Catalysts for Olefin Epoxidation: A literature review 1985-86," *Catalysts in Chemistry*, Vol. 21, No. 3, (1987) pp. 106–112. A number of oxidation processes are briefly mentioned, including ones involving iron and manganese porphyrin catalysts, primarily with a concentration on processes producing epoxides. The oxidation of cyclohexane to cyclohexanol and cyclohexanone by molecular oxygen catalyzed by ruthenium (III)-ethylenediaminetetraacetic acid in the presence and absence of the micelle cetyltrimethylammonium bromide (CTAB) is reported by M. M. Taqui Kahn, et al. in "Ru(III)-EDTA Catalyzed Oxidation of Cyclohexane by Molecular Oxygen," *Journal of Molecular Catalysis*, Vol. 45, (1988) pp. 51–56. The rate of oxidation was found to increase in the presence of CTAB. Similarly of interest is T. Lau, et al., "Ruthenium Catalysed Oxidation of Alkanes with Alkylhydroperoxides," *J. Chem. Soc., Chem. Commun.*, (1988) pp. 1406–1407, which reports that cis-[Ru(II)(L)-2(OH$_2$)$_2$]$^{2+}$ complexes may catalyze the oxidation of saturated hydrocarbons, such as cyclohexane, hexane and heptane, to alcohols and ketones by t-butylhydroperoxide. The L in the ruthenium catalyst formula may be substituted 2,2'-bipyridines of 1,10-phenanthrolines.

Of somewhat more pertinent interest are a number of publications describing research focussing on metalloporphyrin catalysts to make alcohols and ketones. For example, D. Mansuy, et al. in "Metalloporphyrin-Catalyzed Hydroxylation of Cyclohexane by Alkyl Hydroperoxides: Pronounced Efficiency of Iron-Porphyrins," *Angew. Chem. Int. Ed. Engl.*, Vol 19, No. 11, (1980) pp. 909–910, describe the catalyzed hydroxylation of non-activated alkanes, either by molecular oxygen in the presence of a reducing agent, or by two-electron oxidants. The researchers noted that the metalloporphyrins studied fell into three classes. First, the Cu(II)-, Ni(II)-, Zn(II)-, Mg(II)-, V(IV)- and Ti(IV)-porphyrins were found to be completely inactive under the reaction conditions used. The Co(TPP) and Os(TPP)(CO)(PY) compounds were found to catalyze cyclohexane oxidation, the former giving even a slightly faster reaction and better yields than Fe(TPP)(Cl), but both showing decreasing activity over time. The third group of Fe- and Mn(TPP)Cl were found to be true catalysts. A related study is reported in D. Mansuy, et al., "Alkane Hydroxylation Catalyzed by Metalloporphyrins: Evidence for Different Active Oxygen Species with Alkylhydroperoxides and Iodosobenzene as Oxidants," *Tetrahedron Letters*, Vol. 23, No. 27, (1982) pp. 2781-2784. The comparative examination of cyclohexane and n-heptane hydroxylations by cumylhydroperoxide and iodosobenzene, catalyzed by various metalloporphyrins, indicated that different active oxygen species, presumably the cumyloxy radical and a metal-oxo intermediate were involved in these reactions. The metals used in the catalysts included iron, manganese, cobalt, rhodium and chromium.

Azido(tetraphenylporphyrinato) complexes Of $Cr^{III}$, $Mn^{III}$ and $Fe^{III}$ are found to catalyze the selective, low temperature hydroxylation of isobutane with molecular oxygen, according to P. E. Ellis, et al. in "Effect of Axial Azide on the Selective, Low Temperature Metalloporphyrin-catalysed Reactions of Isobutane with Molecular Oxygen," *J. Chem. Soc., Chem. Commun.*, 1989, pp. 1187-88.

P. H. J. Carlsen in "Ruthenium Catalyzed Oxidation of Alkanes," *Synthetic Communications*, Vol. 17, No. 1, (1987) pp. 19-23 reports the use of a $RuCl_3$ catalyst in a solvent system containing $CCl_4$-$CH_3CN$-$H_2O$ and using sodium metaperiodate as the stoichiometric oxidation agent to oxidize a series of alkyl substituted alkanes. Norbornane and bicyclo[2.2.2]octane are oxidized to the corresponding ketone and adamantane is transformed to 1-adamantol. Another article of interest is Y. V. Geletti, et al., "Oxidation of Saturated Hydrocarbons by Hydrogen Peroxide in Pyridine Solution Catalysed by Copper and Iron Perchlorates," *J. Chem. Soc., Chem. Comm.*, (1988) pp. 936-937. The hydrocarbons used are cyclohexane and 2-methylbutane, which yield the ketone and alcohol with alkyl radicals not being intermediates.

Additionally of note is U.S. Pat. No. 4,459,427 which teaches that a mixture of the alcohol and ketone derivatives of alkanes may be produced by reacting the alkane with a hydrocarbyl hydroperoxide, e.g. t-butyl hydroperoxide in the presence of a catalyst The catalyst may be an iron or manganese square planar complex having heterocyclic nitrogen-donor ligands, e.g. a porphyrin or phthalocyanine complex, which complex has either no axial ligands, for example, the lower valency or cationic complex, or an axial ligand which is non-coordinating or weakly-coordinating. Weakly coordinating ligands are defined as ligands having a coordinating power less than that of the chloride anion. The alkane employed is preferably a linear or branched alkane having from about 2 to 20 carbon atoms. Suitable complexes having no axial ligands are either neutral iron (II) and manganese (II) complexes, e.g. Fe(II)(TPP) and Mn(II)(TPP) or iron (III) and manganese (III) cationic complexes, such as [Fe(III)(TPP)]+ and [Mn(III)(TPP)]+.

Finally, European Patent Application No. 0274909 A2 is of interest. It submits that hydrocarbons, particularly lower molecular weight alkanes and cycloalkanes, may be oxidized with air or oxygen to form products such as alcohols, ketones and the like selectively in high yields when there is employed as the catalyst a highly active azide- or nitride-activated metal coordination complex having the structure:

where M is a transition metal; the circle represents a ligand, and R is azide or nitride. Certain dimeric forms of these catalysts may also be employed. It is also discussed that Group IV through VIII transition metal nitrides are also effective oxidation catalysts for lower molecular weight hydrocarbons, such as alkanes. The discussion therein is also directed to certain novel azide-activated metal coordination complex catalysts, per se.

It will be appreciated that in the processes briefly described above, a wide variety of products is often achieved. In many of the reports on those processes, it was stated that a mixture of all possible products resulted. Thus, it would be advantageous if processes could be developed which would maximize the yield to a particularly useful product, in turn, by minimizing the yield to the other by-products. It would also be preferred that the reaction be able to be run at ambient temperature with catalysts that are readily obtainable so that the synthesis might be relatively simple and economical.

SUMMARY OF THE INVENTION

Accordingly, it is an object of the present invention to provide a process for the production of detergent range alcohols and ketones from hydrocarbons and peroxides using transition metal porphyrin catalysts.

It is another object of the present invention to provide a process for the production of detergent range alcohols and ketones that produces a minimum of by-products.

Another object of the invention to provide a method for making detergent range alcohols and ketones at ambient temperature and pressure conditions.

In carrying out these and other objects of the invention, there is provided, in one form, a process for the production of detergent range alcohols and ketones comprising reacting an alkane having from about 10 to 18 carbon atoms with a hydroperoxide selected from the group comprising cumene hydroperoxide, tertiary butyl hydroperoxide and mixtures thereof, in the presence of a transition metal porphyrin catalyst selected from the group consisting of transition metal phthalocyanines, transition metal metalloporphines and mixtures thereof where the transition metal is selected from the group consisting of iron, manganese, cobalt and mixtures thereof.

DETAILED DESCRIPTION OF THE INVENTION

It has been discovered that detergent range alcohols and ketones may be produced from hydrocarbons and a hydroperoxide using metal porphyrin catalysts, particularly transition metal phthalocyanine and metalloporphyrin catalysts. In general, alkanes are difficult to react, hence, in many of the oxidation techniques discussed previously and those herein, a preparation step is required to provide an appropriate feedstock or co-reactant. In a preparation step, a second hydrocarbon containing a tertiary carbon, different from that used to make the alcohols and ketones, such as cumene or tertiary-butane, is oxidized to the corresponding hydroperoxide. Next, the hydroperoxide is reacted with the hydrocarbon in the presence of the catalyst, in accordance with the present invention. After isolation of the alcohols and ketones by distillation, the by-product carbinol derived from the hydroperoxide is reduced to the hydrocarbon and recycled to the hydroperoxide formation step. The overall result is the production of alcohols and ketones with a minimum of byproduct formation. For example, dodecanones and dodecanols are produced when n-dodecane is the starting, first hydrocarbon. The alcohols and ketones produced are useful intermediates for surfactants and detergents.

The second step, the reaction of interest, may be outlined as follows:

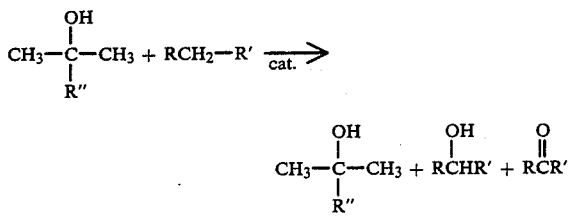

where R and R' are alkyl groups, taken together and with the central CH$_2$ group having 10 to 18 carbon atoms, and where R" is an alkyl or aryl group of one to ten carbon atoms. The RCH$_2$R' group may be a linear or branched hydrocarbon. In one aspect, these hydrocarbons have 11 to 16 carbon atoms.

Examples of suitable hydroperoxides are cumene hydroperoxide, t-butyl hydroperoxide and mixtures thereof; and examples of suitable alkanes are decane, undecane, n-dodecane, tridecane, tetradecane and the like, although it will be appreciated that the inventive process is not limited to these illustrative examples As mentioned, the hydroperoxides may be prepared by the conventional air oxidation of the corresponding hydrocarbon. In one aspect, good results are obtained when the hydroperoxide is concentrated at least in the range of 60 to 90%. With respect to the hydrocarbons, pure hydrocarbons or mixtures may be employed.

A wide variety of transition metal porphyrin catalysts have been discovered as being suitable for the reaction In one aspect, phthalocyanines and metalloporphines are preferred. Specific examples of suitable catalysts include, but are not necessarily limited to, iron phthalocyanine, ferrous phthalocyanine, chloroferric phthalocyanine, iron (II) meso-tetraphenyl porphine chloride, manganese (III) tetraphenyl porphine acetate, cobalt (II) meso-tetraphenyl porphine, and mixtures thereof. Interestingly, nickel phthalocyanine does not give the desired alcohol and/or ketone product. It has also been discovered that certain ligands, oxidants and other additives, when used in conjunction with these catalyst systems, may provide beneficial results. For example, it has been discovered that the metalloporphines mentioned above work particularly well with imidazoles as ligands. Further, chloroferric phthalocyanine may use lithium borate as a ligand, or may use potassium superoxide or iodosylbenzene as an additive to advantage. Alkali metal perchlorates, such as sodium perchlorate have also been discovered as useful additives when employed with chloroferric phthalocyanine. When potassium superoxide, KO$_2$, is employed together with the chloroferric phthalocyanine catalyst tetrabutyl ammonium bromide may be used to advantage. In general, these additives improve the yield to the ketone/alcohol mixture. Other suitable superoxides that may be of use include, but are not limited to rubidium superoxide and cesium superoxide. Although the superoxides and iodosyl benzene are both known as oxidants, it is not believed that they act as oxidants in this case. One possible way in which these additives might function is as "reactive ligands" in that they may perform as the borates or imidazoles, i.e. as ligands, but reactive to some extent.

The reaction conditions advantageous for this process are a temperature range from about 10° to 180° C., preferably from 20° to 80° C. Atmospheric pressures are preferred for convenience, but elevated pressures may be suitable as well with certain modifications to the process. It has been found that with some of the catalysts, such as chloroferric phthalocyanine and ferrous phthalocyanine, that at higher temperatures, about 80° C. or more that more alcohol than ketone is produced, whereas at lower temperatures, about 20° C. or so, and lower that the ratio shifts to the ketone. This discovery is contrary to expectation since one skilled in the art would expect that more ketone, the more highly oxidized species, would be present at the higher temperatures.

As noted previously, an advantage of the process is that the carbinol may be converted back to the corresponding hydrocarbon and recycled to the oxidation step to produce more hydroperoxide. To take cumene hydroperoxide as a specific example, the by-product dimethyl phenyl carbinol may be reduced to cumene using known technology and recycled.

The invention is useful for the preparation of higher molecular weight alcohols and ketones, which are useful chemical intermediates for surfactants and detergents. Additionally, there is a minimum of by-product derived from the hydrocarbon. Various esters of the alcohols are useful lubricants, and some serve as plasticizers for plastics As an added bonus, the reaction takes place at ambient temperatures, although, as noted, the ratio of alcohol to ketone may be adjusted using the reaction temperature. The invention will be described further with reference to the following illustrative, detailed examples.

PROCEDURE 1A

This procedure will describe the preparation of the hydroperoxide, using cumene hydroperoxide (CHP) as an example. Cumene (190.0 g. 99% pure provided by Aldrich Chemical Co.) and cumene hydroperoxide (10.0 g., 85.7% pure provided by Aldrich Chemical Co.) were charged to a 250 ml resin flask equipped with stirrer, thermometer, heating mantle (Therm-O-Watch temperature regulator), water cooled condenser, and gas-sparging tube. The reaction mixture was purged with nitrogen and heated to the desired temperature (±2° C.). A zero-time sample was withdrawn for gas chromatography (GC) analysis and air (or pure oxygen) sparged through the reaction mixture at the required rate using a Gilmont flowmeter. The reaction mixture was heated at the desired temperature (±2° C.) and small samples (0.2-0.5 g.) withdrawn at various times. The samples were flushed with nitrogen and placed in small sealed vials until analysis by GC. At the end of the reaction, the reaction mixture was cooled to ambient temperature (while nitrogen was flushed through the solution) and then placed in a tared bottle. GC analysis was on a Hewlett-Packard 5890 gas chromatograph. The column was a 0.53 mm×30 meter fused silica capillary column (DB-17, 50% phenyl methyl silicone). The conditions 80°–275° C. after 4.0 min. 10# He 190 cc split, 0.5 μl injection, 80° C. injection temperature. Some typical results are shown in Table IA. The examples are numbered starting at Example 101 to easily distinguish them from the more important inventive examples, which begin at "Example 1". Cumene may be distilled off to produce CHP of the desired concentration for Procedure 2, also called the second step.

TABLE IA

Peroxidation of Cumene

| Ex. No. | Time (hrs.) | Temp. °C. | Fl Rt.[1] (ml/m) | Oxygen form | Cumene Conv. % | Selectivity %[2] | | | | |
|---|---|---|---|---|---|---|---|---|---|---|
| | | | | | | CHP | DMPC | ACETP | MeSTY | UNK. |
| 101 | 1.00 | 110.0 | 100.0 | A | 1.63 | 90.31 | 6.85 | 1.77 | 0.53 | 0.00 |
| 102 | 2.00 | 110.0 | 100.0 | A | 4.47 | 94.00 | 3.99 | 1.09 | 0.34 | 0.06 |
| 103 | 3.00 | 110.0 | 100.0 | A | 7.90 | 95.13 | 3.17 | 0.86 | 0.25 | 0.07 |
| 104 | 4.00 | 110.0 | 100.0 | A | 11.82 | 94.63 | 3.68 | 0.92 | 0.21 | 0.06 |
| 105 | 5.00 | 110.0 | 100.0 | A | 15.78 | 93.91 | 4.12 | 1.23 | 0.18 | 0.06 |
| 106 | 6.00 | 110.0 | 100.0 | A | 20.52 | 92.69 | 4.65 | 1.90 | 0.15 | 0.10 |
| 107 | 7.00 | 110.0 | 100.0 | A | 24.19 | 92.19 | 5.21 | 1.44 | 0.14 | 0.10 |
| 108 | 0.50 | 120.0 | 100.0 | A | 1.76 | 92.79 | 4.57 | 1.54 | 0.50 | 0.00 |
| 109 | 1.00 | 120.0 | 100.0 | A | 3.57 | 92.97 | 4.37 | 1.62 | 0.46 | 0.07 |
| 110 | 2.00 | 120.0 | 100.0 | A | 7.63 | 92.78 | 4.56 | 1.64 | 0.41 | 0.09 |
| 111 | 3.00 | 120.0 | 100.0 | A | 12.54 | 92.73 | 4.77 | 1.54 | 0.35 | 0.11 |
| 112 | 4.00 | 120.0 | 100.0 | A | 16.57 | 91.66 | 5.55 | 1.77 | 0.33 | 0.17 |
| 113 | 5.00 | 120.0 | 100.0 | A | 20.67 | 90.55 | 6.45 | 2.03 | 0.29 | 0.17 |
| 114 | 6.00 | 120.0 | 100.0 | A | 24.98 | 88.78 | 7.21 | 2.35 | 0.26 | 0.32 |
| 115 | 7.00 | 120.0 | 100.0 | A | 28.88 | 85.07 | 6.38 | 6.80 | 0.24 | 0.35 |
| 116 | 0.50 | 130.0 | 100.0 | A | 1.32 | 90.70 | 5.30 | 2.09 | 1.22 | 0.00 |
| 117 | 1.00 | 130.0 | 100.0 | A | 3.18 | 91.44 | 4.82 | 1.98 | 1.02 | 0.16 |
| 118 | 1.50 | 130.0 | 100.0 | A | 5.33 | 90.69 | 5.44 | 2.28 | 0.90 | 0.17 |
| 119 | 2.00 | 130.0 | 100.0 | A | 7.89 | 90.16 | 5.90 | 2.47 | 0.79 | 0.18 |
| 120 | 3.00 | 130.0 | 100.0 | A | 12.43 | 86.91 | 7.48 | 3.47 | 0.70 | 0.22 |
| 121 | 4.00 | 130.0 | 100.0 | A | 17.53 | 85.07 | 9.63 | 3.91 | 0.59 | 0.29 |
| 122 | 5.00 | 130.0 | 100.0 | A | 23.14 | 81.44 | 11.53 | 4.61 | 0.47 | 0.50 |
| 123 | 6.00 | 130.0 | 100.0 | A | 28.31 | 78.99 | 13.97 | 5.21 | 0.38 | 0.64 |
| 124 | 1.00 | 140.0 | 100.0 | A | 4.56 | 87.48 | 7.28 | 3.34 | 1.38 | 0.00 |
| 125 | 2.00 | 140.0 | 100.0 | A | 9.48 | 80.96 | 12.15 | 5.10 | 1.26 | 0.00 |
| 126 | 1.00 | 110.0 | 200.0 | B | 1.41 | 96.65 | 2.24 | 0.56 | 0.00 | 0.00 |
| 127 | 2.00 | 110.0 | 200.0 | B | 4.71 | 95.12 | 3.21 | 0.86 | 0.21 | 0.05 |
| 128 | 3.00 | 110.0 | 200.0 | B | 9.16 | 94.47 | 3.88 | 0.94 | 0.16 | 0.04 |
| 129 | 4.00 | 110.0 | 200.0 | B | 13.62 | 93.82 | 4.45 | 1.04 | 0.14 | 0.05 |
| 130 | 5.00 | 110.0 | 200.0 | B | 18.74 | 93.17 | 5.08 | 1.09 | 0.12 | 0.04 |
| 131 | 6.00 | 110.0 | 200.0 | B | 23.19 | 92.44 | 5.42 | 1.48 | 0.11 | 0.05 |
| 132 | 1.00 | 120.0 | 200.0 | B | 6.22 | 93.72 | 4.05 | 1.35 | 0.28 | 0.06 |
| 133 | 2.00 | 120.0 | 200.0 | B | 15.67 | 91.15 | 5.47 | 1.74 | 0.18 | 0.07 |
| 134 | 3.00 | 120.0 | 200.0 | B | 26.74 | 89.99 | 7.19 | 2.13 | 0.13 | 0.07 |
| 135 | 4.00 | 120.0 | 200.0 | B | 37.51 | 87.09 | 8.84 | 2.46 | 0.10 | 0.09 |
| 136 | 5.00 | 120.0 | 200.0 | B | 46.41 | 85.83 | 13.19 | 0.00 | 0.12 | 0.16 |
| 137 | 6.00 | 120.0 | 200.0 | B | 53.16 | 82.16 | 15.76 | 0.00 | 0.20 | 0.40 |
| 138 | 1.00 | 130.0 | 200.0 | B | 14.51 | 90.57 | 6.12 | 2.46 | 0.24 | 0.08 |
| 139 | 2.00 | 130.0 | 200.0 | B | 36.36 | 85.27 | 9.06 | 4.90 | 0.12 | 0.14 |
| 140 | 3.00 | 130.0 | 200.0 | B | 55.21 | 79.77 | 14.61 | 4.38 | 0.12 | 0.26 |
| 141 | 4.00 | 130.0 | 200.0 | B | 64.87 | 67.65 | 12.48 | 15.21 | 0.49 | 2.21 |
| 142 | 5.00 | 130.0 | 200.0 | B | 65.57 | 50.07 | 22.72 | 9.94 | 1.40 | 10.86 |
| 143 | 1.00 | 140.0 | 200.0 | B | 25.92 | 86.01 | 8.99 | 4.03 | 0.26 | 0.21 |
| 144 | 2.00 | 140.0 | 200.0 | B | 53.19 | 75.31 | 11.98 | 11.41 | 0.16 | 0.54 |
| 145 | 3.00 | 140.0 | 200.0 | B | 64.33 | 59.88 | 27.95 | 7.67 | 0.55 | 1.93 |

[1] CHP = cumene hydroperoxide, DMPC = dimethylphenylcarbinol, ACETP = acetophenone, MeSTY = α-methylstyrene, UNK. = sum of unknowns with retention higher than CHP.
[2] Flow rate for air (A) or pure oxygen (B)

PROCEDURE 1B

A mixture of tert-butyl hydroperoxide, tert-butyl alcohol and acetone in a ratio of 65:34:1, equivalent to 5–6% isobutane conversion, and finely divided sodium pyrophosphate (0.01 wt. % basis total) was charged to the autoclave through a small vent hole near the top of the reactor. The autoclave was then sealed and isobutane pressured in. The mixture was then heated to the desired temperature. The stirring rate was 300 rpm. Oxygen was added in ~1 g. increments until a pressure of 150–200 psi over autogenous was reached. Oxygen was then added only after the pressure had dropped 50 psi. The reaction was continued for the desired time and near the end of the reaction, no more oxygen was added so that a large excess of oxygen would not be present to create an explosive mixture. The reaction was cooled as rapidly as possible to ambient temperature and the contents pressured out into a tared stainless steel bomb with 300 psi nitrogen. The weight % products were determined by GC analysis of bomb contents.

TABLE IB

Isobutane Oxidation at 145° C.

| Ex. | Time (Hr.) | IB (Wt. %) | THBP (Wt. %) | TBA (Wt. %) | Acetone[1] (Wt. %) |
|---|---|---|---|---|---|
| 146 | 2.0 | 73.915 | 18.114 | 7.678 | 0.155 |
| 147 | 2.5 | 69.745 | 20.847 | 9.021 | 0.197 |
| 148 | 3.5 | 59.101 | 26.964 | 13.188 | 0.406 |
| 149 | 4.0 | 55.917 | 28.347 | 14.972 | 0.460 |
| 150 | 2.0 | 74.712 | 17.751 | 7.188 | 0.135 |
| 151 | 2.5 | 70.923 | 19.815 | 8.833 | 0.285 |
| 152 | 3.0 | 65.161 | 23.277 | 10.858 | 0.271 |
| 153 | 4.0 | 55.307 | 28.742 | 15.247 | 0.427 |
| 154 | 4.0 | 55.207 | 28.494 | 15.526 | 0.448 |
| 155 | 2.0 | 75.814 | 17.130 | 6.850 | 0.122 |
| 156 | 3.0 | 66.495 | 22.604 | 10.453 | 0.251 |
| 157 | 4.0 | 55.593 | 28.188 | 13.720 | 0.422 |
| 158 | 4.0 | 53.980 | 28.728 | 15.613 | 0.499 |
| 159 | 1.0 | 83.183 | 12.252 | 4.468 | 0.037 |
| 160 | 3.0 | 63.706 | 23.693 | 11.716 | 0.309 |

TABLE IB-continued

Isobutane Oxidation at 145° C.

| Ex. | Time (Hr.) | IB (Wt. %) | THBP (Wt. %) | TBA (Wt. %) | Acetone[1] (Wt. %) |
|---|---|---|---|---|---|
| 161 | 3.16 | 62.065 | 24.478 | 12.352 | 0.332 |

[1]Acetone plus methanol, but methanol is usually low (20-15% of acetone).

PROCEDURE 2

This procedure will outline the inventive process for producing detergent range alcohols and ketones. N-Dodecane (50.0 g.) and the indicated catalyst(s) were charged to a 250 ml flask equipped with stirrer, dropping funnel and thermometer. Cumene hydroperoxide (80%) was added slowly to the stirred reaction mixture over several hours. The temperature was maintained by the use of a water bath or a heating mantle. At the end of the reaction, the mixture was filtered and analyzed by GC and/or GC/IR (infrared spectroscopy). The results are shown in the following Table II. The alcohols and ketones may be isolated by distillation. The by-products dimethyl phenyl carbinol and α-methyl styrene may be reduced and recycled.

TABLE II

Detergent Range Ketones and Alcohols from Higher Molecular Weight Hydrocarbons and Cumene Hydroperoxide Using Phthalocyanine and Metalloporphine as Catalysts

| Ex. | Catalyst(s)[1] | Wt., grams | Time, hours | Temp. °C. | Wt. % $C_{12}$ Products Ketone | Wt. % $C_{12}$ Products Alcohol |
|---|---|---|---|---|---|---|
| 1 | FePCYCl<br>IM | 0.10<br>0.07 | 24.0 | 30 | 5.02 | 1.42 |
| 2 | FePCYCl<br>IM | 0.10<br>0.025 | 23.0 | 30 | 4.39 | 0.98 |
| 3 | Fe(II)PCY<br>IM | 0.10<br>0.05 | 23.0 | 30 | 4.57 | 0.90 |
| 4 | FePCYCl | 0.10 | 7.0 | 60 | 3.04 | 1.04 |
| 5 | FePCYCl<br>IM | 0.10<br>0.05 | 7.0 | 60 | 2.61 | 1.24 |
| 6 | Ni(II)PCY<br>IM | 0.10<br>0.05 | 24.0 | 30 | 0 | 0 |
| 7 | Fe(AcAc)₃ | 0.10 | 26.0 | 26 | 0.161 | 0 |
| 8 | FePCYCl | 0.10 | 24.0 | 26 | 4.40 | 1.00 |
| 9 | Fe(III)TPPCl<br>IM | 0.05<br>0.025 | 25.0 | 30 | 1.75 | 0.24 |
| 10 | Mn(III)TPPOAc<br>IM | 0.05<br>0.025 | 23.0 | 30 | 1.47 | 0.328 |
| 11 | Co(II)TPP<br>IM | 0.05<br>0.025 | 26.0 | 30 | 1.18 | 0.31 |

[1]FePCY = chloroferric phthalocyanine
FE(II)PCY = ferrous phthalocyanine
Ni(II)PCY = nickel (II) phthalocyanine
Fe(AcAc)₃ = ferric acetyl acetonate
Fe(III)TPPCl = iron (III) m-tetraphenyl porphine
Mn(III)TPPOAc = manganese (III) m-tetraphenyl porphine acetate
Co(II)TPP = cobalt (II) m-tetraphenyl porphine
IM = imidazole Interestingly, the nickel (II) phthalocyanine catalyst used in Example 6 gave neither the desired alcohol or ketone, though the iron porphyrins did give the alcohol and ketone products; see Examples 1-5 and 8-11. Also by way of contrast, the iron acetylacetonate catalyst used in Example 7 gave no alcohol and very little ketone.

EXAMPLES 12-20

Use of Chloroferric Phthalocyanine as Catalyst Together with Lithium Borate as an Additive A 250 ml flask was charged with the indicated catalyst(s), n-dodecane (30.0 g.), tert-butyl alcohol (35.0 g.), and this mixture was vigorously stirred. A mixture of 33.0 g. 90% tert-butyl hydroperoxide and 22.0 g. of tert-butyl alcohol were added slowly to this stirred mixture over several hours. All of the reactions were performed at 25° C. and were controlled by means of a water bath. The reactions were stirred for a total of 20 hours and filtered through fluted filter paper. The results shown in Table III were obtained by GPC. Chloroferric phthalocyanine [Fe(III)PCYCl] in quantities of 0.50 g. was used in all of these Examples. It is believed that the lithium borate serves as a ligand in complex with the chloroferric phthalocyanine.

TABLE III

Use of Lithium Borate with Chloroferric Phthalocyanine

| Ex. | LiBO₂, grams | Wt. % TBHP | Wt. % Ketone | Wt. % Alcohol | Wt. % Total | Wt. % DTBP |
|---|---|---|---|---|---|---|
| 12 | None | 0.05 | 4.26 | 0.92 | 5.18 | 1.96 |
| 13 | 0.1 | 0.06 | 6.11 | 1.10 | 7.21 | 1.51 |
| 14 | 0.1 | 0.04 | 6.68 | 0.99 | 7.67 | 1.82 |
| 15 | 0.20 | ≈0 | 6.56 | 1.11 | 7.67 | 1.60 |
| 16 | 0.25 | ≈0 | 7.40 | 1.37 | 8.77 | 1.23 |
| 17 | 0.50 | ≈0 | 6.21 | 1.02 | 7.23 | 1.66 |
| 18 | 0.50 | ≈0 | 6.70 | 1.25 | 7.95 | 1.58 |
| 19 | 1.00 | ≈0 | 7.14 | 1.33 | 8.47 | 1.47 |
| 20 | None | 0.13 | 4.34 | 0.70 | 5.04 | 2.03 |

It will be appreciated that the use of lithium borate in Examples 13-19 give noticeably higher yields to the desired ketones and alcohols than when chloroferric phthalocyanine is employed alone, as in Examples 12 and 20. It is also noted that when the lithium borate was employed in quantities of at least 0.2 g. under these conditions that essentially all of the tert-butyl hydroperoxide (TBHP) is reacted, as seen in Examples 15-19.

EXAMPLES 1T–25T

Temperature Effect on Ketone/Alcohol Ratio

These examples illustrate the discovery that the ratio of ketone/alcohol product may be adjusted by changing the reaction temperature. Two reaction temperatures are used: 20° C. and 80° C. At the higher temperature, more alcohol is formed and at the lower temperature, more ketone is formed. These experiments were all conducted according to the following procedure.

A 250 ml flask equipped with stirrer, thermometer, condenser, and dropping funnel was charged with n-dodecane (30.0 g.), t-butyl alcohol (50.0 g.), and the indicated catalyst(s). t-Butyl hydroperoxide (74.3%, 40.0 g.) was then added over 4 to 5 hours. The mixture was then stirred overnight. The temperature control was within ±5° C. The reaction mixture was then filtered and analyzed by GC. The results are shown in Table IV. The Examples are designated with the notation "T" to indicate that they illustrate the temperature effect of this invention.

using a variety of catalyst systems, at the higher temperature, more alcohol is formed, and at the lower temperature, more ketone is formed.

It is also noted that di-tert-butyl peroxide (DTBP) is a useful by-product of this reaction. DTBP finds commercial use as a free radical initiator.

EXAMPLES 21–28

Addition Time Effect

These Examples will illustrate that when TBHP is added to the stirred reaction mixture over a long time period that chloroferric phthalocyanine (FePCYCl) as the catalyst produces a higher yield of alcohol plus ketone. There is only a small or negligible difference when ferrous phthalocyanine [Fe(II)PCY] is used as a catalyst and long TBHP addition times are used. Procedure: A 250 ml round-bottom flask equipped with water-cooled condenser, thermometer and magnetic stirrer was charged with catalyst, n-dodecane, and tert-butyl alcohol (TBA). The flask was suspended in a water bath to which ice was added from time to time to maintain

TABLE IV

Reaction of tert-Butyl Hydroperoxide with n-Dodecane in the Presence of Chloroferric Phthalocyanine and Ferrous Phthalocyanine

| Ex. | Catalyst I | (g.) | Cat. II | (g.) | Time (hr) | Temp (°C.) | Wt. % TBHP | Wt. % Ket. | Wt. % Alc. | Wt. % Total | Wt % Ket/ Wt % Alc. | Wt. % DTBP |
|---|---|---|---|---|---|---|---|---|---|---|---|---|
| 1T | FePCYCl | 0.25 | — | — | 20 | 25 | — | 5.75 | 1.16 | 6.91 | 4.96 | 1.80 |
| 2T | FePCYCl | 0.50 | CuPCY | 0.10 | 20 | 25 | ~0 | 7.53 | 1.54 | 9.07 | 4.89 | 1.18 |
| 3T | CuPCY | 0.50 | — | — | 20 | 25 | 17.77 | 0.094 | 0 | 0.094 | — | 0.12 |
| 4T | FePCYCl | 0.50 | — | — | 20 | 80 | ~0 | 3.27 | 5.27 | 8.54 | 0.62 | 0.16 |
| 5T | FePCYCl | 0.50 | CuPCY | 0.05 | 20 | 80 | ~0 | 3.98 | 5.94 | 9.92 | 0.67 | 0.19 |
| 6T | FePCYCl | 0.50 | CuPCY | 0.05 | 20 | 25 | ~0 | 8.16 | 1.77 | 9.93 | 4.61 | 1.19 |
| 7T | FePCYCl | 0.50 | CuPCY | 0.10 | 20 | 25 | ~0 | 7.19 | 1.26 | 8.45 | 5.70 | 1.33 |
| 8T | Fe(AcAc)$_3$ | 0.50 | — | — | 20 | 80 | 14.74 | 0.50 | 0.36 | 0.86 | — | 0.11 |
| 9T | Fe(AcAc)$_3$ | 0.50 | Cu(AcAc)$_2$ | 0.10 | 20 | 80 | 11.51 | 1.44 | 0.98 | 2.42 | — | 0.26 |
| 10T | FePCYCl | 0.25 | — | — | 20 | 25 | ~0 | 6.20 | 1.19 | 7.39 | 5.21 | 1.63 |
| 11T | FePCYCl | 0.25 | Cu(AcAc)$_2$ | 0.05 | 20 | 25 | ~0 | 5.81 | 1.03 | 6.84 | 5.64 | 1.69 |
| 12T | Fe(AcAc)$_3$ | 0.50 | Cu(AcAc)$_2$ | 0.05 | 20 | 80 | 7.16 | 2.75 | 1.45 | 4.20 | 1.90 | 0.40 |
| 13T | Fe(II)PCY | 0.50 | — | — | 20 | 80 | ~0 | 3.56 | 6.05 | 9.61 | 0.59 | 0.15 |
| 14T | Fe(II)PCY | 0.50 | Cu(AcAc)$_2$ | 0.05 | 20 | 80 | ~0 | 3.37 | 4.80 | 8.17 | 0.70 | 0.20 |
| 15T | Fe(II)PCY | 0.50 | — | — | 20 | 25 | ~0 | 8.00 | 1.63 | 9.63 | 4.90 | 1.10 |
| 16T | Fe(II)PCY | 0.50 | Cu(AcAc)$_2$ | 0.05 | 20 | 25 | ~0 | 7.67 | 1.58 | 9.25 | 4.85 | 1.21 |
| 17T | Fe(II)PCY | 0.50 | Cu(II)PCY | 0.05 | 20 | 25 | ~0 | 8.76 | 2.06 | 10.82 | 4.25 | 0.86 |
| 18T | Fe(II)PCY | 0.50 | Cu(OAc)$_2$ | 0.05 | 20 | 25 | ~0 | 7.50 | 1.61 | 9.11 | 4.66 | 0.95 |
| 19T | Fe(II)PCY | 0.50 | Cu(II)PCY | 0.05 | 20 | 80 | ~0 | 3.81 | 5.31 | 9.12 | 0.72 | 0.18 |
| 20T | Fe(II)PCY | 0.50 | Cu(II)PCY | 0.05 | 20 | 25 | ~0 | 7.44 | 1.57 | 9.01 | 4.75 | 1.21 |
| 21T | Fe(II)PCY | 1.00 | — | — | 20 | 25 | ~0 | 6.70 | 2.42 | 9.12 | 2.76 | 1.02 |
| 22T | Fe(II)PCY | 0.50 | — | — | 20 | 80 | n/a | 0 | 0 | 0 | n/a | 8.93* |
| 23T | Fe(II)PCY | 0.25 | — | — | 20 | 25 | ~0 | 6.61 | 1.33 | 7.94 | 4.97 | 1.63 |
| 24T | Fe(II)PCY | 0.10 | — | — | 20 | 25 | ~0 | 5.38 | 1.08 | 6.46 | 4.98 | 1.95 |
| 25T | Fe(II)PCY | 0.04 | — | — | 20 | 25 | 0.28 | 4.12 | 0.82 | 4.94 | 5.02 | 2.18 |

*15.0 g. DTBP charged instead of TBHP.

With reference to Table IV, compare Examples 1T and 10T which are run at the lower temperature of 20° C. and give a ratio of wt. % ketone:wt. % alcohol of 4.96 and 5.21, respectively, with Example 4T run at the higher temperature of 80° C. which gives a ratio of 0.62 indicative of a greater alcohol proportion. Similarly, compare low temperature Examples 6T and 7T with hotter Example 5T; the ratios are 4.61 and 5.70 compared with 0.67. Further, low temperature Examples 15T and 16T with comparable high temperature Example 13T; as well as low temperature Examples 17T and 20T with higher temperature Example 19T. In all cases, the temperature. Tert-Butyl hydroperoxide (TBHP) was then added to the stirred reaction mixture by means of a syringe pump. At the end of the addition, the reaction was stirred for 5–10 hours more at ambient temperature and then filtered. In this instance, the term "ambient temperature" is 30° C. ±5° C. Also, in every Example, the amount of n-dodecane was 30.0 grams, the amount of TBA was 57.0 g., the amount of 90% TBHP was 33.0 g., and the amount of catalyst was 5.0 g. The products were determined by GC, and the data are presented in Table V.

TABLE V

Reaction of n-Dodecane with TBHP at Long TBHP Addition Times

| Ex. | Catalyst | Rate TBA Addn. (ml/hr) | Products, wt. % | | | TBHP (wt. %) Remaining |
|---|---|---|---|---|---|---|
| | | | Ketones | Alcohols | Total | |
| 21 | Fe(III)PCYCl | 0.458 | 5.548 | 2.623 | 8.171 | 2.376 |

TABLE V-continued

Reaction of n-Dodecane with TBHP at Long TBHP Addition Times

| Ex. | Catalyst | Rate TBA Addn. (ml/hr) | Products, wt. % Ketones | Products, wt. % Alcohols | Products, wt. % Total | TBHP (wt. %) Remaining |
|---|---|---|---|---|---|---|
| 22 | Fe(II)PCY | 0.458 | 3.229 | 5.652 | 8.881 | 3.434 |
| 23 | Fe(III)PCYCl | 2.292 | 3.851 | 0.690 | 4.541 | 2.371 |
| 24 | Fe(II)PCY | 2.292 | 4.032 | 3.381 | 7.413 | 0.789 |
| 25 | Fe(III)PCYCl | 4.584 | 2.546 | 0.756 | 3.302 | 1.272 |
| 26 | Fe(II)PCY | 4.584 | 5.220 | 3.226 | 8.446 | 0.114 |
| 27 | Fe(III)PCYCl | 11.46 | 3.673 | 0.688 | 4.361 | ~0 |
| 28 | Fe(II)PCY | 11.46 | 6.127 | 2.716 | 8.843 | 0.071 |

EXAMPLES 29–42

Effect of Iodosylbenzene as Additive

These are further Examples of the preparation of detergent range alcohols and ketones from n-dodecane and tert-butyl hydroperoxide using chloroferric phthalocyanine as the catalyst. It has been further discovered that when small amounts of an additive, such as iodosylbenzene are added to the reaction mixture, the rate of reaction is increased significantly. In this series of Examples, iodosylbenzene is the only additive employed and FePCYCl is the only catalyst used. The abbreviation "Inh. time" refers to the inhibition time, which is the time required for the reaction to proceed at least 1%. The term $t_{\frac{1}{2}}$ refers to the half-life in minutes. The weight percent of products was determined by GC. The results are reported in Table VI, and it is noted which of the following two procedures was used.

Procedure A: TBA and the catalyst were charged to a 250 ml, 3-necked round bottom flask equipped with a stirrer, thermometer, water cooled condenser, and water bath. A tube led from the top of the condenser to a water filled gas-buret. TBHP was added all at once to the stirred mixture, the flask sealed, and the volume of gas (oxygen) given off at specified time intervals noted. A semilog plot of V-V∞ versus time gave a pseudo first order rate constant ($10^3$k min$^{-1}$). The products were determined by GC analysis of the filtered reactor effluent.

Procedure B: The same as the procedure used for the Examples of Table III, herein. The TBHP was added over a period of about 4 to about 6 hours.

TABLE VI

Reaction of 90% TBHP with n-Dodecane in the Presence of Chloroferric Phthalocyanine and Iodosylbenzene at Ambient Temperature.

| Ex. | C12 (g) | 90% TBHP (g) | TBA (g) | Cat. (g) | IB (g) | Acetone | TBA | C-12 | DTBP | Ketones | Alcohols | Inh. Time (min) | $10^3$k min$^{-1}$ | $t_{\frac{1}{2}}$ (min) | Procedure |
|---|---|---|---|---|---|---|---|---|---|---|---|---|---|---|---|
| 29 | 0.0 | 5.0 | 18.0 | 0.20 | 0.04 | 0.825 | 95.045 | 0.0 | 3.793 | 0.0 | 0.0 | 10 | 38.5 | 18 | A |
| 30 | 0.0 | 5.0 | 18.0 | 0.20 | 0.01 | 0.516 | 95.956 | 0.0 | 3.303 | 0.0 | 0.0 | 12 | 34.7 | 20 | A |
| 31 | 0.0 | 5.0 | 18.0 | 0.20 | None | 0.424 | 96.505 | 0.0 | 2.909 | 0.0 | 0.0 | 10 | 19.8 | 35 | A |
| 32 | 5.0 | 5.0 | 13.0 | 0.20 | None | 0.371 | 72.705 | 20.16 | 2.502 | 2.365 | 0.326 | 9 | 6.48 | 107 | A |
| 33 | 5.0 | 5.0 | 13.0 | 0.20 | 0.005 | 0.005 | 0.327 | 73.55 | 19.60 | 2.581 | 2.512 | 0.338 | 3.5 | 34.7 | A |
| 34 | 30.0 | 55.0 | 35.0 | 0.50 | 0.25 | 0.443 | 69.393 | 16.31 | 1.387 | 6.477 | 1.965 | — | — | — | A |
| 35 | 30.0 | 55.0 | 35.0 | 0.50 | 0.10 | 0.398 | 68.674 | 16.78 | 1.243 | 6.334 | 2.161 | — | — | — | B |
| 36 | 5.0 | 5.0 | 13.0 | 0.20 | 0.01 | 0.333 | 73.965 | 19.47 | 2.491 | 1.999 | 0.291 | 5 | 36.5 | 19 | A |
| 37 | 5.0 | 5.0 | 13.0 | 0.20 | 0.02 | 0.339 | 72.850 | 20.14 | 2.596 | 2.507 | 0.313 | 4 | 38.5 | 18 | A |
| 38 | 5.0 | 5.0 | 13.0 | 0.20 | 0.10 | 0.355 | 72.944 | 19.97 | 2.574 | 2.574 | 0.331 | 4 | 38.5 | 18 | A |
| 39 | 30.0 | 55.0 | 35.0 | 0.50 | 0.25 | 0.005 | 72.011 | 15.62 | 1.915 | 5.654 | 1.131 | — | — | — | B |
| 40 | 30.0 | 55.0 | 35.0 | 0.50 | 0.10 | 0.458 | 69.516 | 18.96 | 2.050 | 5.238 | 0.784 | — | — | — | B |
| 41 | 5.0 | 5.0 | 13.0 | 0.20 | 0.04 | 0.352 | 74.083 | 19.10 | 2.633 | 2.439 | 0.304 | 2 | 38.5 | 18 | A |
| 42 | 5.0 | 5.0 | 13.0 | 0.20 | None | 0.299 | 73.245 | 19.96 | 2.412 | 2.487 | 0.324 | 5 | 7.37 | 94 | A |

EXAMPLES 43–57

Use of Sodium Perchlorate as an Additive

Examples 43–57 will illustrate the production of detergent range alcohols and ketones from n-dodecane and tert-butyl hydroperoxide using a chloroferric phthalocyanine catalyst and sodium perchlorate as an additive. Sodium perchlorate is also used as an oxidant. However, in this case it might be better thought of as a ligand, but if so as at least a somewhat "reactive" ligand. It has been additionally discovered that the rate of reaction increases significantly when small amounts of sodium perchlorate are added to the reaction mixture. The abbreviations used in Table VI are employed here as well. The term "R" refers to the correlation coefficient. The term "PYDiCr" refers to pyridinium dichromate. The procedure used was the same as that employed for Examples 29–42.

TABLE VII

Reaction of TBHP with n-Dodecane in the Presence of Chloroferric Phthalocyanine and Sodium Perchlorate

| Ex. | C-12 (g) | TBA (g) | Cat. (g) | Additive | Additive (g) | Inh. time (min) | $10^3$k min$^{-1}$ | R | $t_{\frac{1}{2}}$ (min) |
|---|---|---|---|---|---|---|---|---|---|
| 43 | 0.0 | 18.0 | 0.20 | NaClO$_4$ | 0.10 | 4 | 59.9 | 0.978 | 11.7 |
| 44 | 0.0 | 18.0 | 0.20 | NaBF$_4$ | 0.10 | — | 18.4 | 0.960 | 37.6 |
| 45 | 0.0 | 18.0 | 0.20 | None | 0.0 | — | 13.6 | 0.962 | 51.0 |
| 46 | 0.0 | 18.0 | 0.50 | NaBF$_4$ | 0.10 | — | 34.8 | 0.965 | 19.9 |
| 47 | 0.0 | 18.0 | 0.20 | PTYDiCr | 0.05 | — | 6.53 | 0.997 | 106 |
| 48 | 5.0 | 13.0 | 0.20 | None | 0.0 | — | 6.71 | 0.994 | 103 |
| 49 | 5.0 | 13.0 | 0.20 | NaClO$_4$ | 0.05 | — | 34.3 | 0.973 | 20.2 |

TABLE VII-continued

Reaction of TBHP with n-Dodecane in the Presence of Chloroferric Phthalocyanine and Sodium Perchlorate

| Ex. | C-12 (g) | TBA (g) | Cat. (g) | Additive | Additive (g) | Inh. time (min) | $10^3k$ $min^{-1}$ | R | $t_{\frac{1}{2}}$ (min) |
|---|---|---|---|---|---|---|---|---|---|
| 50 | 5.0 | 13.0 | 0.20 | NaClO$_4$ | 0.02 | — | 30.4 | 0.978 | 22.8 |
| 51 | 5.0 | 13.0 | 0.20 | NaClO$_4$ | 0.02 | 4 | 71.7 | 0.876 | 9.7 |
| 52 | 5.0 | 13.0 | 0.20 | NaClO$_4$ | 0.01 | <1 | 132 | 0.962 | 5.3 |
| 53 | 5.0 | 13.0 | 0.20 | NaClO$_4$ | 0.005 | 2 | 71.1 | 0.988 | 9.8 |
| 54 | 5.0 | 13.0 | 0.20 | NaClO$_4$ | 0.10 | 1 | 111 | 0.966 | 6.3 |
| 55 | 5.0 | 13.0 | 0.20 | NaClO$_4$ | 0.50 | <1 | 113 | 0.937 | 6.1 |
| 56 | 5.0 | 13.0 | 0.20 | None | 0.0 | 5 | 20.3 | 0.982 | 34.2 |
| 57 | 5.0 | 13.0 | 0.40 | None | 0.0 | 4 | 20.0 | 0.986 | 34.6 |

TABLE VIII

Results of Reactions of TBHP with n-Dodecane in the Presence of Chloroferric Phthalocyanine and Sodium Perchlorate

| | | | Products, Weight Percent, by GC | | | | |
|---|---|---|---|---|---|---|---|
| Ex. | Acetone | TBA | DTBP | TBHP | Ketones | Alcohols | K + A Total |
| 43 | 0.264 | 97.148 | 2.484 | 0.0 | — | — | — |
| 44 | 0.518 | 96.120 | 3.045 | 0.046 | — | — | — |
| 45 | 0.607 | 96.114 | 3.202 | 0.0 | — | — | — |
| 46 | 0.346 | 96.472 | 3.033 | 0.0 | — | — | — |
| 47 | 0.475 | 96.129 | 3.095 | 0.0 | — | — | — |
| 48 | 0.135 | 65.102 | 1.919 | 0.0 | 3.771 | 0.487 | 4.258 |
| 49 | 0.290 | 75.532 | 2.676 | 0.059 | 2.691 | 0.406 | 3.097 |
| 50 | 0.133 | 68.371 | 2.261 | 0.101 | 2.416 | 0.433 | 2.849 |
| 51 | 0.328 | 75.504 | 2.670 | 0.0 | 2.697 | 0.391 | 3.088 |
| 52 | 0.245 | 70.693 | 2.456 | 0.0 | 2.846 | 0.430 | 3.276 |
| 53 | 0.235 | 71.204 | 2.492 | 0.0 | 2.809 | 0.402 | 3.211 |
| 54 | 0.313 | 72.734 | 2.701 | 0.0 | 2.556 | 0.376 | 2.932 |
| 55 | 0.254 | 70.911 | 2.562 | 0.0 | 2.888 | 0.416 | 3.304 |
| 56 | 0.200 | 67.230 | 2.227 | 0.0 | 3.375 | 0.790 | 4.165 |
| 57 | 0.153 | 53.969 | 1.832 | 0.0 | 4.778 | 1.200 | 5.978 |

EXAMPLES 58-63

Use of Potassium Superoxide as an Additive

These Examples will demonstrate that potassium superoxide is a useful additive when used with the chloroferric phthalocyanine catalyst of the present invention. It is expected that rubidium and cesium superoxides would also be useful in this regard. High yields of the ketone/alcohol mixture may be obtained. The procedure was as follows: A 250-ml flask was charged with catalyst(s), n-dodecane (30.0 g), tert-butyl alcohol (35.0 g.), and this mixture was vigorously stirred. In Examples 58-63, 0.50 g. of Fe(III)PCYCl catalyst was used throughout. A mixture of 33.0 g. 90% tert-butyl hydroperoxide and 22.0 g. of tert-butyl alcohol was added slowly to this stirred mixture over several hours. The reactions at 25° C. were controlled by means of a water bath. The reactions at 80° C. were controlled by means of a Therm-O-Watch temperature regulator. The reactions were stirred for a total of 20 hours and filtered through fluted filter paper. The results shown in Table IX below were obtained by GPC.

Again, although potassium superoxide is often an oxidant, it is suspected that it may be acting as a ligand in this case. If it is acting as a ligand, it is not acting in the same way as imidazole or lithium borate. It may be functioning as a kind of reactive ligand, but this is not known for certain.

TABLE IX

Reaction of 90% TBHP with n-Dodecane in the Presence of Ferric Phthalocyanine and Potassium Superoxide

| | | | | Products, Wt. Percent by GPC | | | | |
|---|---|---|---|---|---|---|---|---|
| Ex. | Additive | Additive (g) | Temp (°C.) | TBHP | Ketone | Alcohol | Total | Ketone/ Alcohol | DTBP |
| 58 | KO$_2$ | 0.10 | 25 | ~0 | 6.01 | 1.12 | 7.13 | 5.36 | 1.81 |
| 59 | KO$_2$ | 0.30 | 25 | ~0 | 6.52 | 1.19 | 7.71 | 5.45 | 1.68 |
| 60 | KO$_2$ | 0.50 | 25 | ~0 | 6.44 | 1.19 | 7.63 | 5.41 | 1.71 |
| 61 | KO$_2$ | 0.30 | 80 | ~0 | 2.94 | 5.49 | 8.43 | 0.54 | 0.18 |
| 62 | — | — | 25 | 0.05 | 4.26 | 0.92 | 5.19 | 4.63 | 1.96 |
| 63 | K$_2$S$_2$O$_8$ | 0.50 | 25 | 0.11 | 5.14 | 0.90 | 6.04 | 5.71 | 1.77 |

EXAMPLES 64-71

The Use of Tetrabutyl Ammonium Bromide as a Phase Transfer Catalyst

These Examples will illustrate the use of tetrabutyl ammonium bromide (TBAB) in conjunction with an additive, such as potassium superoxide (KO$_2$) from the previous Examples 58-63. In the presence of potassium superoxide and TBAB as well as the chloroferric phthalocyanine catalyst, an increased yield of detergent range alcohols and ketones is obtained.

In the procedure of Examples 64-71, a 250-ml flask was charged with catalyst(s), n-dodecane (30.0 g.), and tert-butyl alcohol (35.0 g.), and this mixture was vigorously stirred. A mixture of 33.0 g. 90% tert-butyl hydroperoxide and 22.0 g. of tert-butyl alcohol was added slowly to this stirred mixture over several hours. The reactions were all conducted at 25° C., and temperature was controlled by means of a water bath. The reactions were stirred for a total of 20 hours and filtered through fluted filter paper. The results shown in Table X below were obtained by GPC. Example 62 which uses no additive is shown for comparison.

TABLE X

Reaction of 90% TBHP with n-Dodecane in the Presence of Ferric Phthalocyanine, Potassium Superoxide, and Tetrabutyl Ammonium Bromide

| Ex. | Catalyst | Cat. (g) | Additive | Additive (g) | TBHP | Ketone | Alcohol | Total | Ketone/ Alcohol | DTBP |
|---|---|---|---|---|---|---|---|---|---|---|
| 64 | Fe(III)PCYCl | 0.50 | CTMAC | 0.25 | 0.05 | 4.46 | 0.70 | 5.16 | 6.37 | 2.07 |
| 65 | Fe(III)PCYCl | 0.50 | TBAB | 0.25 | ~0 | 6.00 | 1.09 | 7.09 | 5.50 | 1.57 |
| 66 | Fe(III)PCYCl | 0.50 | THAB | 0.25 | 0.25 | 4.89 | 0.85 | 5.74 | 5.75 | 1.85 |
| 67 | Fe(III)PCYCl | 0.50 | MBTPPC | 0.25 | 0.17 | 4.05 | 0.70 | 4.75 | 5.78 | 2.18 |
| 68 | Fe(III)PCYCl | 0.50 | KO$_2$ CTMAC | 0.50 0.25 | 0.05 | 7.26 | 0.95 | 8.21 | 7.64 | 1.28 |
| 69 | Fe(III)PCYCl | 0.50 | KO$_2$ TBAB | 0.50 0.25 | ~0 | 7.03 | 1.41 | 8.44 | 4.99 | 1.43 |
| 70 | Fe(III)PCYCl | 0.50 | KO$_2$ THAB | 0.50 0.25 | 0.07 | 6.93 | 1.31 | 8.24 | 5.29 | 1.36 |
| 62 | Fe(III)PCYCl | 0.50 | — | — | 0.05 | 4.26 | 0.92 | 5.18 | 4.63 | 1.96 |
| 71 | KO$_2$ | 2.00 | THAB | 0.25 | 14.17 | ~0 | ~0 | ~0 | — | 0.06 |

Many modifications may be made in the process of this invention without departing from the spirit and scope thereof which are defined only in the appended claims. For example, one skilled in the art may discover a new additive or reaction condition which may not be explicitly recited herein, but which is nevertheless anticipated, and which would give desirable results.

GLOSSARY

| GLOSSARY | |
|---|---|
| CHP | Cumene hydroperoxide |
| CTMAC | Cetyl trimethylammonium chloride |
| Cu(AcAc)$_2$ | Copper (II) acetylacetonate |
| Cu(OAc)$_2$ | Copper (II) acetate |
| CuPCY | Cuprous phthalocyanine |
| Cu(II)PCY | Copper (II) phthalocyanine |
| DTBP | Di-tert-butyl peroxide |
| Fe(AcAc)$_3$ | Iron (III) acetylacetonate |
| Fe(II)PCY | Ferrous phthalocyanine |
| FePCYCl | Chloroferric phthalocyanine, also denoted as Fe(III)PCYCl |
| IB | Iodosylbenzene |
| IM | Imidazole |
| MBTPPC | Methylbenzyl triphenyl phosphonium chloride |
| PYDiCr | Pyridinium dichromate |
| TBA | tert-Butyl alcohol |
| TBAB | Tetrabutyl ammonium bromide |
| TBHP | tert-Butyl hydroperoxide |
| THAB | Tetrahexyl ammonium bromide |

We claim:

1. A process for the production of a mixture of detergent range alcohols and ketones having from about 10 to 18 carbon atoms comprising reacting an alkane having from about 10 to 18 carbon atoms with a hydroperoxide at a 718 temperature in the range of from about 10° to 180° C. in the presence of a transition metal porphyrin catalyst selected from the group consisting of ferrous phthalocyanine, chloroferric phthalocyanine, iron (II) meso-tetraphenyl porphine chloride, manganese (II) tetraphenyl porphine acetate, cobalt (II) meso-tetraphenyl porphine, and mixtures thereof.

2. The process of claim 1 where the hydroperoxide is selected from the group consisting of cumene hydroperoxide, tertiary butyl hydroperoxide, and mixtures thereof.

3. The process of claim 1 where transition metal porphyrin catalyst is chloroferric phthalocyanine in the additional presence of an additive selected from the group consisting of alkali metal superoxides, alkali metal perchlorates, iodosylbenzene, and mixtures thereof.

4. The process of claim 3 where the reaction is homogeneous, where an alkali metal superoxide is the additive and where tetrabutyl ammonium bromide is present.

5. A process for producing a ratio of detergent range alcohols to detergent range ketones having from about 10 to 18 carbon atoms comprising:
   reacting an alkane having from about 10 to 18 carbon atoms with a hydroperoxide having from about 3 to 10 carbon atoms in the presence of an iron porphyrin catalyst selected from the group consisting of chloroferric phthalocyanine; ferrous phthalocyanine and mixtures thereof; and
   adjusting the temperature of the reaction such that as the temperature is increased, the selectivity to alcohol increases, and as the temperature is decreased, the selectivity to ketone increases, where the temperature of the reaction ranges from about 20° to about 80° C.

6. The process of claim 5 where a ligand is additionally present, where the ligand is selected from the group consisting of imidazoles, lithium borate and mixtures thereof.

7. The process of claim 5 where an additive is additionally present, where the additive is selected from the group consisting of alkali metal perchlorates, alkali metal superoxides, iodosylbenzene and mixtures thereof.

8. The process of claim 7 where the reaction is homogeneous, where the additive is an alkali metal superoxide and where tetrabutyl ammonium bromide is additionally present.

9. A process for the production of detergent range alcohols and ketones having from about 10 to 18 carbon atoms comprising reacting an alkane having from about 10 to 18 carbon atoms with a hydroperoxide having from about 3 to 10 carbon atoms in the presence of an iron porphyrin catalyst selected from the group consisting of chloroferric phthalocyanine, ferrous phthalocyanine and mixtures thereof at a temperature between the range of about 20° and 80° C.

10. A process for the production of a mixture of detergent range alcohols and ketones having from about 10 to 18 carbon atoms comprising reacting an alkane having from about 10 to 18 carbon atoms with a hydroperoxide at a temperature in the range of from about 10° to 180° C. in the presence of a transition metal porphyrin catalyst selected from the group consisting of ferrous phthalocyanine, chloroferric phthalocyanine, iron (II) meso-tetraphenyl porphine chloride, manganese (II) tetraphenyl porphine acetate, cobalt (II) meso-tetraphenyl porphine, and mixtures thereof, where the hydroperoxide is essentially added continuously over a period of time of at least two hours to increase the yield of the detergent range alcohols and ketones.

11. A process for the production of a mixture of detergent range alcohols and ketones having from about 10 to 18 carbon atoms comprising reacting an alkane having from about 10 to 18 carbon atoms with a hydroperoxide at a temperature in the range of from about 10° to 180° C. in the presence of a transition metal porphyrin catalyst selected from the group consisting of ferrous phthalocyanine, chloroferric phthalocyanine, iron (II) meso-tetraphenyl porphine chloride, manganese (II) tetraphenyl porphine acetate, cobalt (II) meso-tetraphenyl porphine, and mixtures thereof, where the transition metal porphyrin catalyst is in the additional presence of a ligand selected from the group consisting of imidazoles, lithium borate and mixtures thereof.

* * * * *

UNITED STATES PATENT AND TRADEMARK OFFICE
CERTIFICATE OF CORRECTION

PATENT NO. : 4,978,799
DATED : December 18, 1990
INVENTOR(S) : John R. Sanderson, Edward T. Marquis, Howard F. Payton It is certified that error appears in the above-identified patent and that said Letters Patent is hereby corrected as shown below:

In claim 1, column 17, line 60, the number "718" should be deleted.

Signed and Sealed this

Sixteenth Day of June, 1992

*Attest:*

DOUGLAS B. COMER

*Attesting Officer*     Acting Commissioner of Patents and Trademarks